(12) United States Patent
Chen et al.

(10) Patent No.: US 9,719,931 B2
(45) Date of Patent: Aug. 1, 2017

(54) SURFACE ENHANCED RAMAN SPECTROSCOPY RESONATOR STRUCTURES AND METHODS OF MAKING SAME

(71) Applicant: Optokey, Inc., Hayward, CA (US)

(72) Inventors: Fanqing Frank Chen, Moraga, CA (US); Robert P. Chebi, San Carlos, CA (US)

(73) Assignee: OPTOKEY, INC., Hayward, CA (US)

( * ) Notice: Subject to any disclaimer, the term of this patent is extended or adjusted under 35 U.S.C. 154(b) by 0 days.

(21) Appl. No.: 14/905,337

(22) PCT Filed: Jul. 15, 2014

(86) PCT No.: PCT/US2014/046720
§ 371 (c)(1),
(2) Date: Jan. 15, 2016

(87) PCT Pub. No.: WO2015/009737
PCT Pub. Date: Jan. 22, 2015

(65) Prior Publication Data
US 2016/0146736 A1    May 26, 2016

Related U.S. Application Data

(60) Provisional application No. 61/847,970, filed on Jul. 18, 2013.

(51) Int. Cl.
*G01J 3/44*     (2006.01)
*G01N 21/65*    (2006.01)
(Continued)

(52) U.S. Cl.
CPC ............. *G01N 21/658* (2013.01); *B82Y 20/00* (2013.01); *B82Y 30/00* (2013.01); *B82Y 40/00* (2013.01)

(58) Field of Classification Search
CPC ...... G01N 21/658; B82Y 20/00; B82Y 30/00; B82Y 40/00
(Continued)

(56) References Cited

U.S. PATENT DOCUMENTS

2006/0034729 A1   2/2006   Poponin
2007/0023621 A1*  2/2007   Blick ..................... B82Y 15/00
                                                    250/251

(Continued)

OTHER PUBLICATIONS

Dutta et al., "Fabrication of Large Area Fishnet Optical Metamaterial Structures Operational at Near-IT Wavelengths," Materials 2010, 3, pp. 5283-5292 (URL:http://www.mdpi.com/1996-1944/3/12/5283/pdf).

(Continued)

*Primary Examiner* — Hina F Ayub
(74) *Attorney, Agent, or Firm* — DLA Piper LLP (US)

(57) ABSTRACT

A nanoplasmonic resonator (NPR) includes a substrate, a first metallic member disposed on the substrate, a second metallic member spaced apart from the first metallic member, and a first insulation layer at least partially disposed between the first and second metallic members. The first insulation layer includes at least one of a notch formed laterally therein such that there is an open gap separating outer edge portions of the first and second metallic members, at least a portion thereof having a toroid shape, and a length extending between the first and second metallic members which are laterally adjacent to each other.

20 Claims, 21 Drawing Sheets

(51) Int. Cl.
    *B82Y 40/00*     (2011.01)
    *B82Y 30/00*     (2011.01)
    *B82Y 20/00*     (2011.01)

(58) Field of Classification Search
    USPC ........................................................ 356/301
    See application file for complete search history.

(56) References Cited

U.S. PATENT DOCUMENTS

| | | |
|---|---|---|
| 2007/0075264 A1 | 4/2007 | Gorrell et al. |
| 2011/0058164 A1 | 3/2011 | Zhang et al. |
| 2011/0063610 A1 | 3/2011 | Ivanov et al. |
| 2012/0136241 A1 | 5/2012 | Chen et al. |
| 2012/0281957 A1 | 11/2012 | Chamanzar et al. |
| 2014/0016127 A1* | 1/2014 | Yamazoe ............... B82Y 20/00 356/301 |
| 2016/0049215 A1* | 2/2016 | Dionne .................. G21K 1/006 250/251 |

OTHER PUBLICATIONS

PCT Search Report and Written Opinion dated Nov. 6, 2014 corresponding to the related PCT Patent Application No. US2014/046720.

* cited by examiner

SURFACE ENHANCED RAMAN SPECTROSCOPY RESONATOR STRUCTURES AND METHODS OF MAKING SAME

RELATED APPLICATIONS

This application claims the benefit of U.S. Provisional Application No. 61/847,970, filed Jul. 18, 2013.

FIELD OF THE INVENTION

The present invention relates to Surface Enhanced Roman Spectroscopy (SERS) for characterizing molecular properties, and more particularly to tunable nanoplasmonic resonators (NPRs) and methods of making NPRs.

BACKGROUND OF THE INVENTION

As shown in FIG. 1, it is presently known to use a nanoplasmonic resonators (NPR) 2 in the form of a thin dielectric layer 4 (e.g. $SiO_2$) sandwiched between two metallic nanodisks 6 on a quartz substrate 8 to enhance SERS (Surface Enhanced Raman Scattering) Raman intensity for the detection of protease and enzyme activity. The NPR 2 results in SERS hot-spots at desired locations and in small dimensions, allowing for multiplexed high-throughput detection and lab-on-chip applications. The resonance frequency of the NPR can be precisely tuned by varying the dielectric layer thickness and the aspect ratio of the NPR. Such NPR and SERS techniques are disclosed in U.S. Pat. No. 8,685,743, which is incorporated herein by reference.

The nanodisk NPRs have been patterned on quartz substrates by electron beam lithography (EBL). However, EBL techniques are time consuming and expensive. Moreover, while disk shaped NPRs have shown to enhance the Raman intensity by a factor of over $6 \times 10^6$, further Raman intensity enhancement is needed.

There is a need for improved techniques in forming NPRs, and there is a need for different NPR structures that further enhance the Raman intensity.

BRIEF SUMMARY OF THE INVENTION

A nanoplasmonic resonator (NPR) includes a substrate, a first metallic member disposed on the substrate, a second metallic member spaced apart from the first metallic member, and a first insulation layer at least partially disposed between the first and second metallic members. The first insulation layer includes at least one of a notch formed laterally therein such that there is an open gap separating outer edge portions of the first and second metallic members, at least a portion thereof having a toroid shape, and a length extending between the first and second metallic members which are laterally adjacent to each other.

A method of fabricating a nanoplasmonic resonator (NPR) include forming a first metallic member on a substrate, forming a second metallic member spaced apart from the first metallic member, and forming a first insulation layer at least partially disposed between the first and second metallic members. The first insulation layer includes at least one of a notch formed laterally therein such that there is an open gap separating outer edge portions of the first and second metallic members, at least a portion thereof having a toroid shape, and a length extending between the first and second metallic members which are laterally adjacent to each other.

Other objects and features of the present invention will become apparent by a review of the specification, claims and appended figures.

BRIEF DESCRIPTION OF THE DRAWINGS

FIGS. 9A-12A and FIGS. 9B-12B are side views and top views, respectively, showing the fabrication of an NPR structure according to a third embodiment.

FIGS. 13A-16A and FIGS. 13B-16B are side views and top views, respectively, showing the fabrication of an NPR structure according to a fourth embodiment.

FIGS. 17A-21A and FIGS. 17B-21B are side views and top views, respectively, showing the fabrication of an NPR structure according to a fifth embodiment.

DETAILED DESCRIPTION OF THE INVENTION

The present invention includes improved NPR structures and fabrication techniques that enhance hot spot formation and performance, and enable fabrication of structures with smaller dimensions.

First Embodiment

Figure 1:
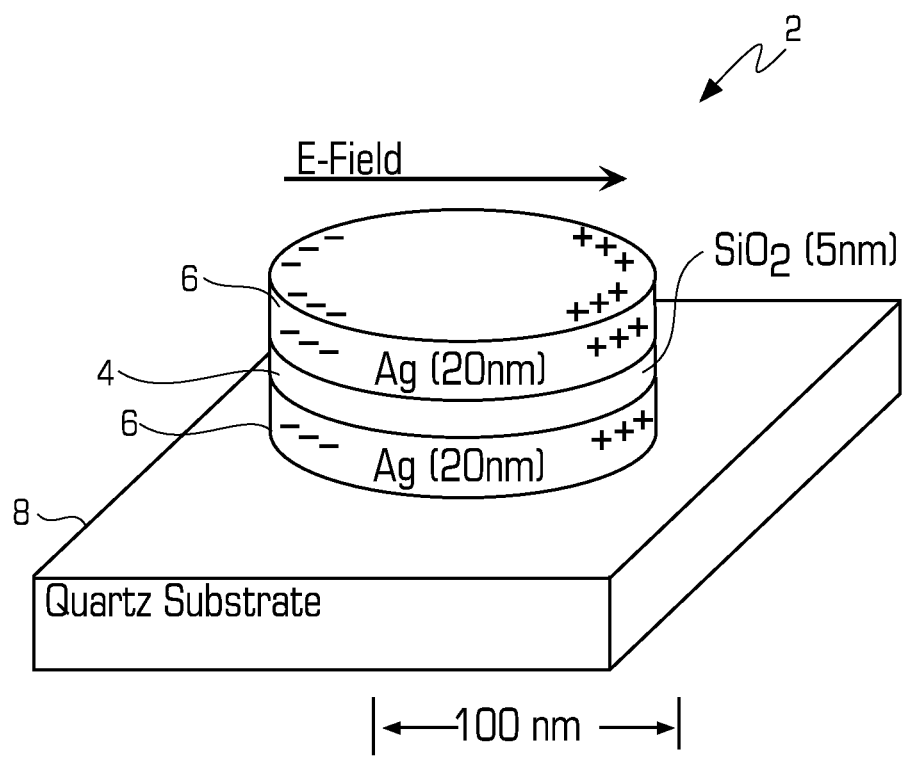
FIG. 1 is a perspective view of a prior art NPR structure.
Figure 2:
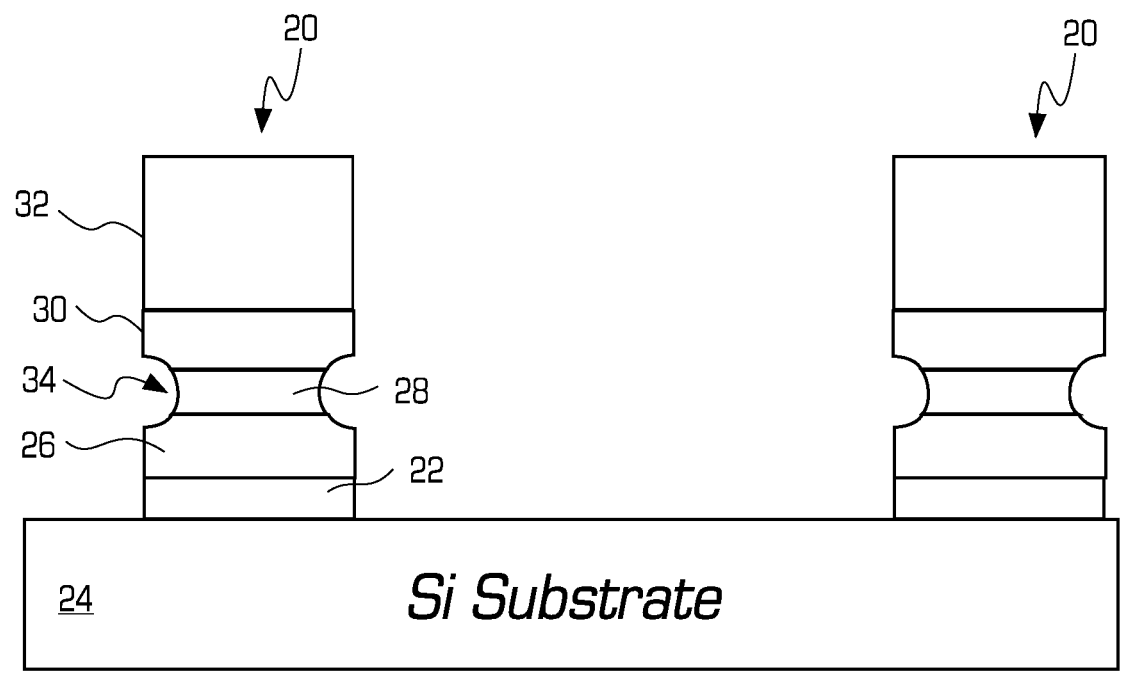
FIGS. 2-4 are side views showing the fabrication of an NPR structure according to a first embodiment.

FIG. 2 illustrates an NPR structure 20 according to a first embodiment of the present invention. NPR structure is fabricated using a photolithographic process that begins by forming a first dielectric layer 22 (e.g. silicon dioxide—$SiO_2$) over a substrate 24 (e.g. Si), followed by forming a first metal layer 26 (e.g. gold or silver) over the first dielectric layer 22, followed by forming a second dielectric layer 28 (e.g. silicon dioxide) over the first metal layer 26, followed by forming a second metal layer 30 (e.g. gold or silver) over the second dielectric layer 28. The metal layers 26 and 30 can be formed by PVD (physical vapor deposition) or ALD (atomic layer deposition). The dielectric layers 22 and 28 can be formed by CVD (chemical vapor deposition) or ALD. The first dielectric layer 22 could instead be formed by thermal oxidation. Photo resist 32 is formed over the second metal layer 30, and patterned using conventional photolithographic masking techniques by selectively exposing portions of the photo resist using a mask, followed by a photo resist etch, which removes some portions of the photo resist (exposing portions of the underlying second metal layer) while leaving other portions of the photo resist intact. An optional photo resist trim etch can be performed to reduce the dimensions of the remaining photo resist below that defined by the masking step. Anisotropic metal, dielectric, metal and dielectric etches are used to remove the exposed portions of the first and second metal layers 26, 30 and the first and second dielectric layers 22, 28. The first dielectric etch can be isotropic or wet, to form inward notches or undercuts 34 in the side edges of second dielectric layer 28, such that there is an open gap 35 separating the outer edge portions of first and second metal layers 26, 30. Exemplary, non-limiting dimension examples include 25 nm thickness for the metal layers 26, 30, a 5 nm thickness of the second dielectric layer 28, and 1 μm or less thickness for the first dielectric layer 22.

Figure 3:
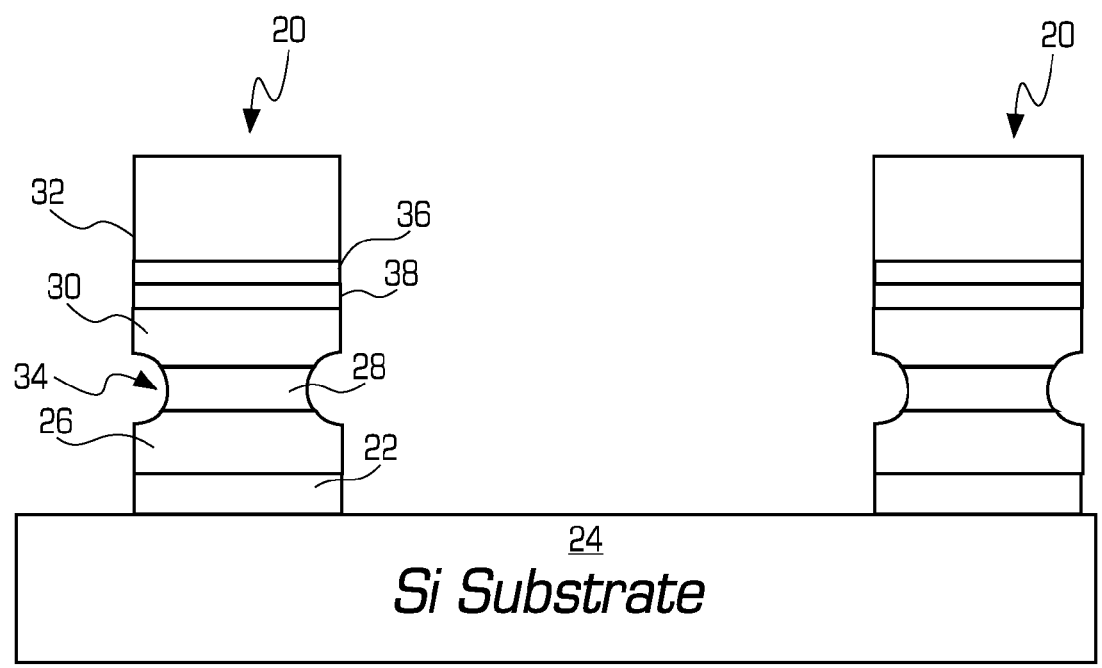

Alternately, an optional carbon layer 36 can be formed on the second metal layer 30, whereby the photo resist 32 is formed on the carbon layer, as shown in FIG. 3. The carbon layer 36 acts as an organic anti-reflective layer so the photo resist is well patterned on exposure. This carbon layer 36 can be used underneath the photo resist for any of the embodiments herein. An additional insulation layer 38 may be formed on the top metal layer 30 (and under the carbon layer 36 if one is used) as a hard mask layer for better etching. One or both of these hard mask layers can be implemented using any appropriate organic, inorganic and/or metallic material(s).

Figure 4:
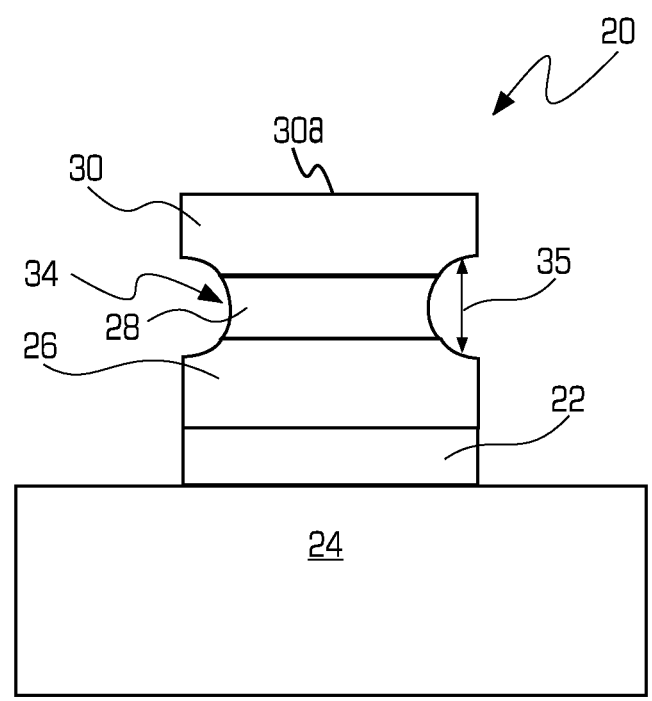
Figure 5:
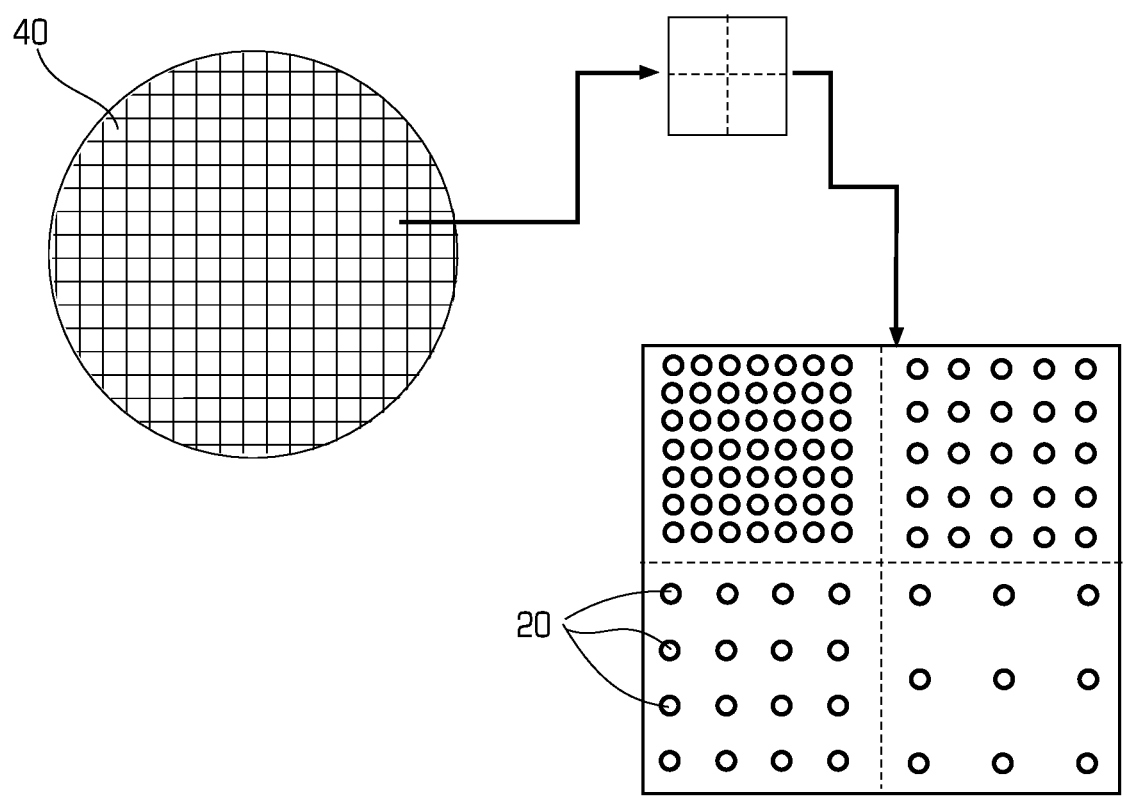
FIG. 5 is a top view of the NPR structure according to the first embodiment.

FIG. 4 shows a single disc stack NPR 20 from FIG. 2 after removal of photo resist 32. Preferably, the NPR 20 disks are oval shaped in the horizontal direction, with the top surface 30a of the second metal layer 30 serving as the surface on which the biomolecule target is applied. Hot spots having the highest electric fields are located at the disk edges at or near the ends of the oval shape (i.e. those portions with the smallest radius of curvature). The notches 34 in the second dielectric layer 28 forming open gaps 35 enhance the electric field hot spots. Using a photolithographic process simplifies the manufacturing process (making it less expensive), and provides accurate and repeatable control over the formation of the NPRs 20 and their critical dimensions. The photolithographic mask could be a mask with discrete apertures (one for each NPR 20). Alternately, the mask could be a series of parallel elongated slits, whereby the photo resist 32 is exposed through the mask, the mask is rotated 90 degrees, and the photo resist 32 is exposed again through the mask, whereby the only portions of the photoresist 32 not exposed by either exposure is the overlap of the two orientations of the elongated slits. While only two metal layers 26, 30 are shown, additional alternating layers of metal and dielectric materials can be formed in the same manner as disclosed above. Preferably, the NPRs are formed together on a single wafer 40 as an array of NPRs 20 of uniform or varying density as shown in FIG. 5.

Second Embodiment

Figure 6:
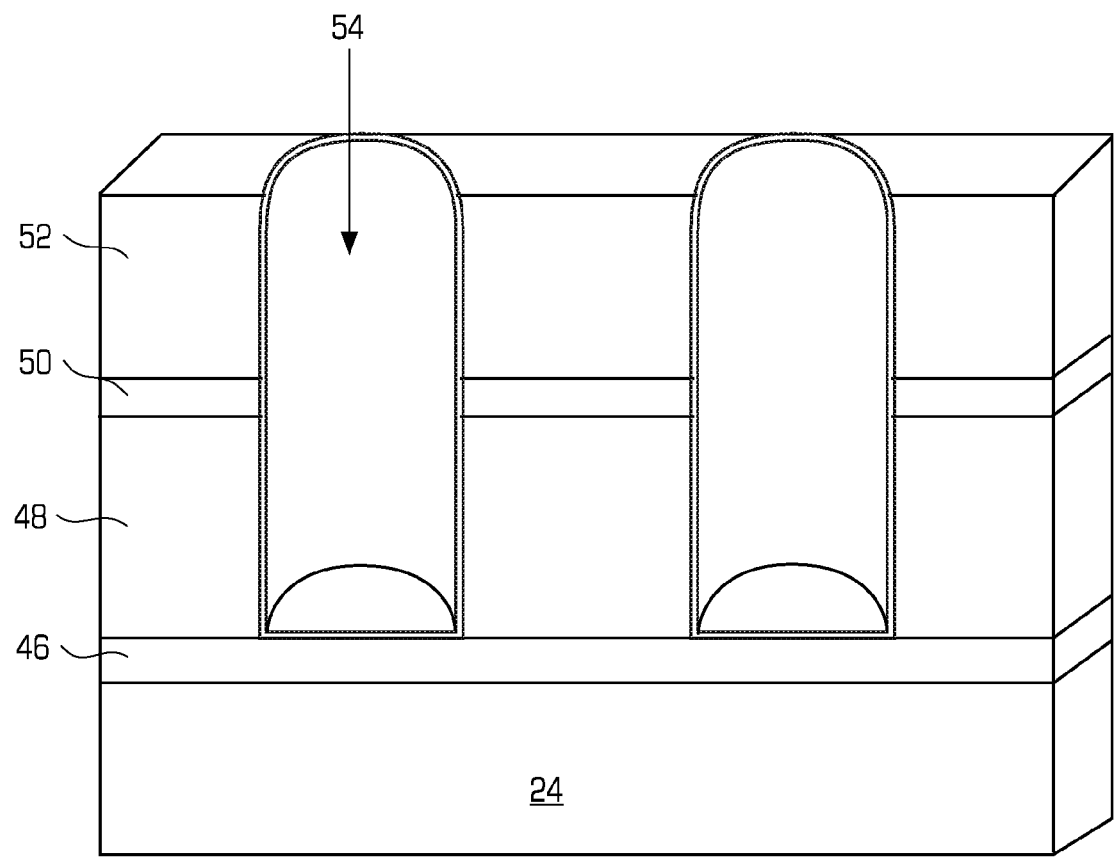
FIGS. 6-8 are side views showing the fabrication of an NPR structure according to a second embodiment.
Figure 7:
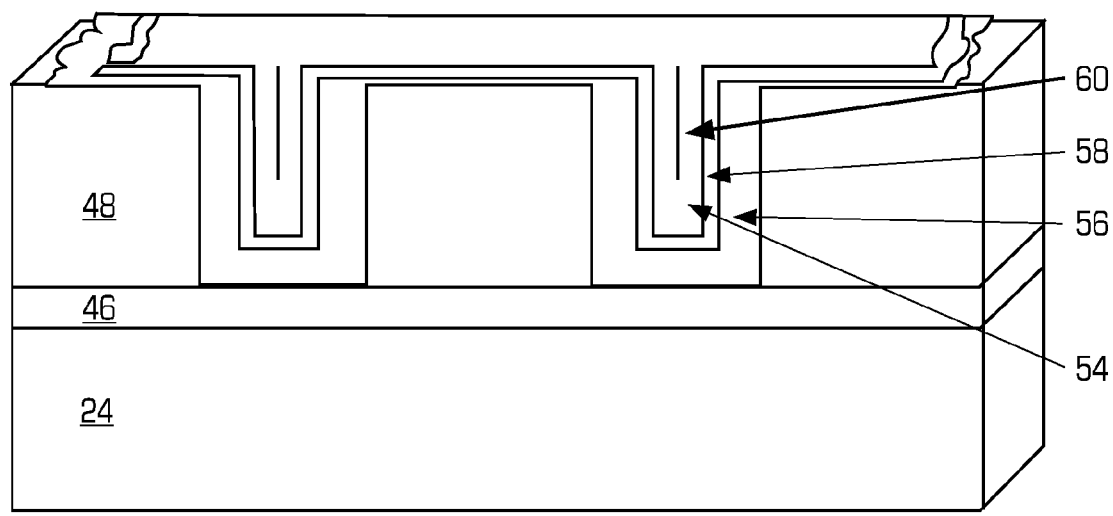
Figure 8:
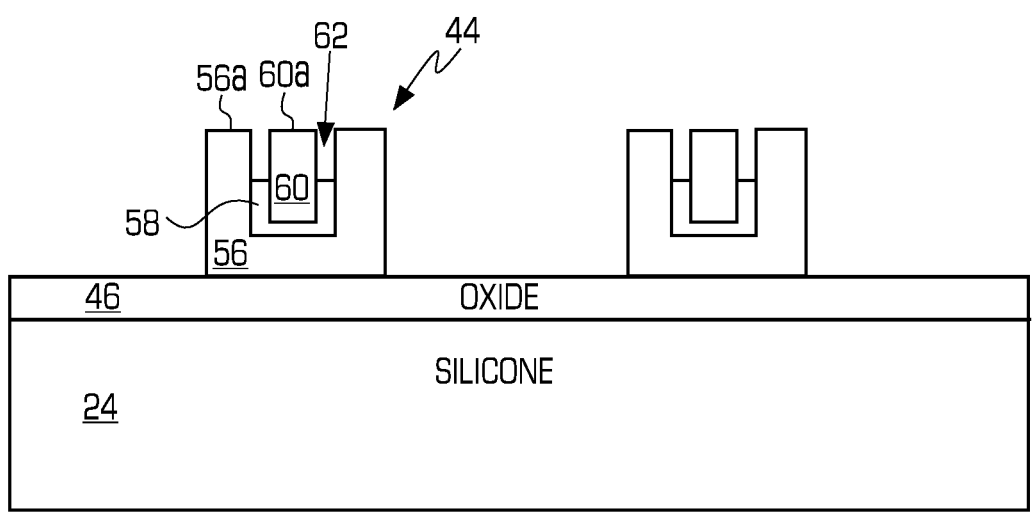

FIGS. 6-8 illustrate the photolithographic process used to form the NPR structure 44 according to a second embodiment. The process begins by performing a pre-oxidation clean on the substrate 24, followed by forming a first dielectric layer 46 (e.g. silicon dioxide—$SiO_2$) over substrate 24 (e.g. Si), for example by thermal oxidation (e.g. 1 μm thick). This is followed by forming a sacrificial layer 48 over the structure (e.g. polymer that is 0.2 μm to 0.3 μm thick). A BARC layer 50 (Bottom Anti-Reflective Coating, e.g. carbon or inorganic material) is formed over the polymer layer 48. Photo resist 52 is formed over the BARC layer 50, and patterned with holes 54 of approximately 50 nm-250 nm in size (patterning includes photolithograph exposure and photo resist etch). BARC and polymer etches are used to extend the holes 54 down to the first dielectric layer 46. The resulting structure is shown in FIG. 6.

The photo resist 52 and BARC layer 50 are then removed, and a first layer of metal 56 (e.g. gold) is deposited on the structure which covers the top surface of the polymer 48 and lines the side and bottom walls of the holes 54 (e.g. 25 nm thickness). A second dielectric layer 58 (e.g. silicon based or HiK) is formed over the first gold layer 56. A second layer of metal 60 (e.g. gold) is formed over the second dielectric layer 58 (e.g. 25 nm thickness), which results in filling the holes 54. The resulting structure is shown in FIG. 7.

A CMP etch is used to remove portions of the gold layers 56, 60 not in the holes 54 and optionally a top portion of the polymer 48 (for example, down to a total polymer height of 55 nm). A polymer etch is used to remove the polymer 48. A wet etch is then used to recess the second dielectric layer 58 in the holes 54, resulting in the final structure of NPR 44 shown in FIG. 8.

The structure of NPR 44 increases the number of edges on which hot spots can form in each NPR. The NPR 44 is formed on dielectric layer (e.g. $SiO_2$) 46, whereby metallic layer 56 (e.g. gold) is disposed on the dielectric layer 46 in discrete blocks. A cavity 62 extends into the top surface of the metallic layer 56. A second metallic layer 60 is disposed inside the cavity but insulated from the first metallic layer 56 by second dielectric layer 58 at the bottom of the cavity 62. Preferably, the second dielectric layer 58 extends part way up toward the top of the cavity 62, leaving an open gap between upper portions of metallic layers 56, 60. Each NPR 44 of this second embodiment includes two metallic top surfaces 56a and 60a (one for each metallic layer), and six annular top surface edges (compared to just one top surface and one annular top surface edge for the disk shaped first embodiment in FIG. 4). This increase in the number of top surfaces and the number of top surface edges provides additional hot spot locations of increased electric field strength.

Third Embodiment

Figure 9A:
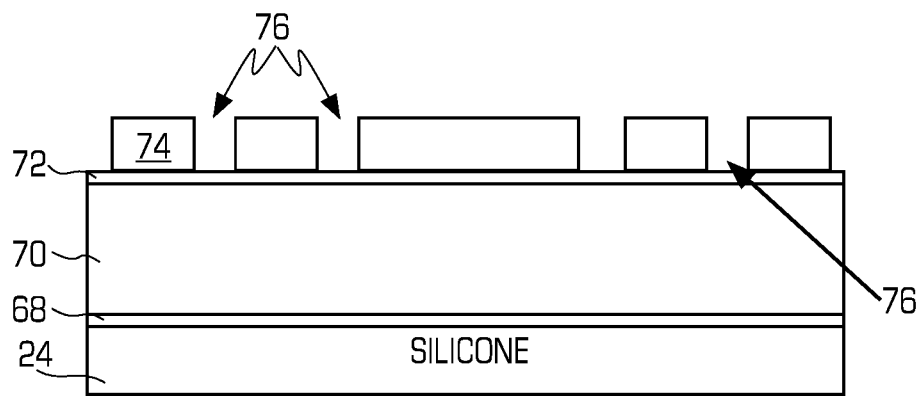
Figure 9B:
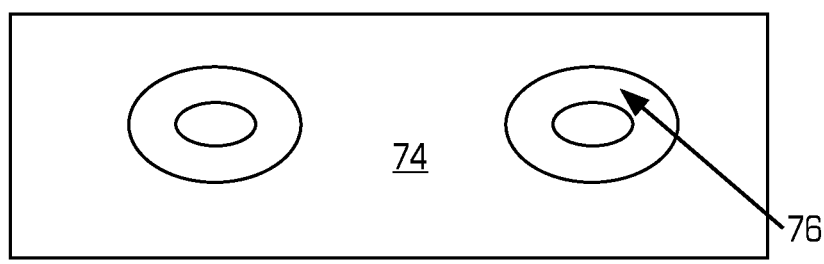
Figure 10A:
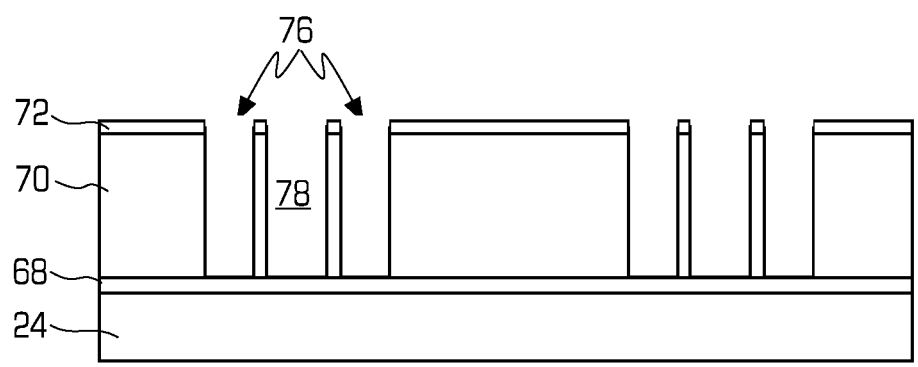
Figure 10B:
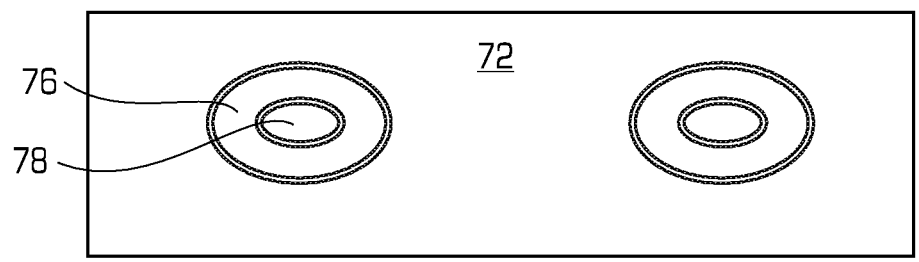

FIGS. 9A-12A and 9B-12B illustrate the photolithographic process used to form the NPR structure 66 according to a third embodiment. The process begins by performing a pre-oxidation clean of substrate 24, following by forming a first dielectric layer 68 (e.g. silicon dioxide—$SiO_2$) over substrate 24 (e.g. Si), for example by thermal oxidation (e.g. 1 μm). This is followed by forming a sacrificial layer 70 over the structure (e.g. polymer that is 50 nm-10 μm thick). A BARC layer 72 is formed over the polymer 70. Photo resist 74 is formed over the BARC layer 72, and patterned with oval shaped cavities 76, as illustrated in FIGS. 9A and 9B (patterning includes photolithograph exposure and resist etch).

BARC and polymer etches are used to extend the cavities 76 defined by the photo resist down through the BARC and polymer layers 72, 70 (i.e. down to and exposing the first dielectric layer 68). The photo resist 74 is then removed. A second photo resist is formed over the BARC layer 72, and patterned with oval shaped holes 78 over the center of the oval shaped cavities 76. BARC and polymer etches are used to extend the holes 78 defined by the second photo resist down through the BARC and polymer layers 72, 70 (i.e. down to and exposing the first dielectric layer 68). The second photo resist is then removed, resulting in the structure shown in FIGS. 10A and 10B.

Figure 11A:
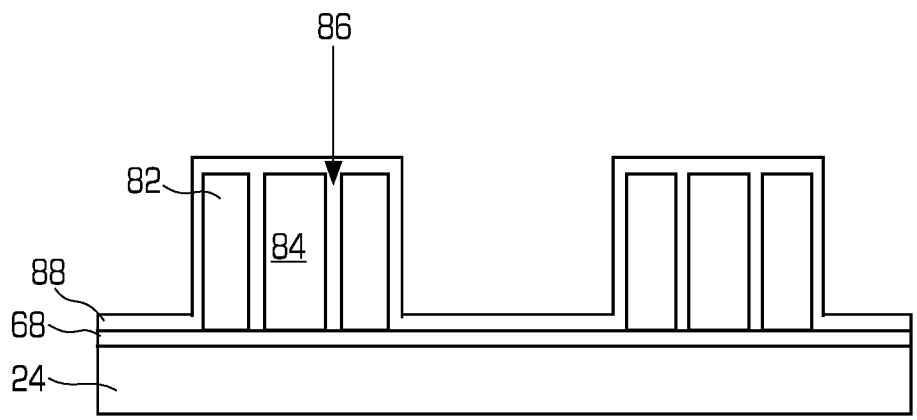
Figure 11B:
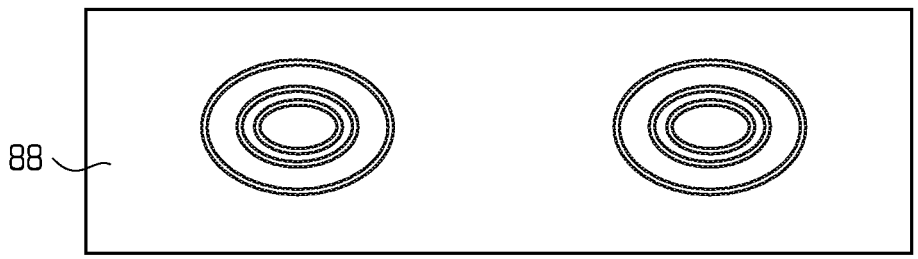
Figure 12A:
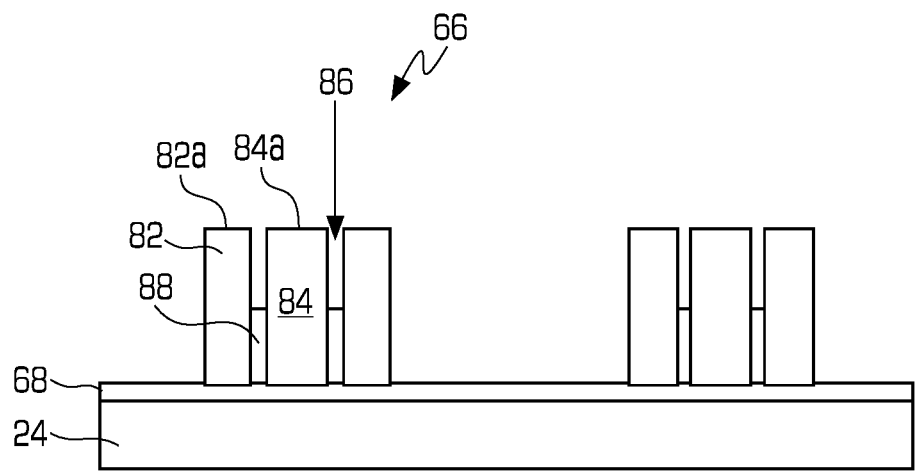
Figure 12B:
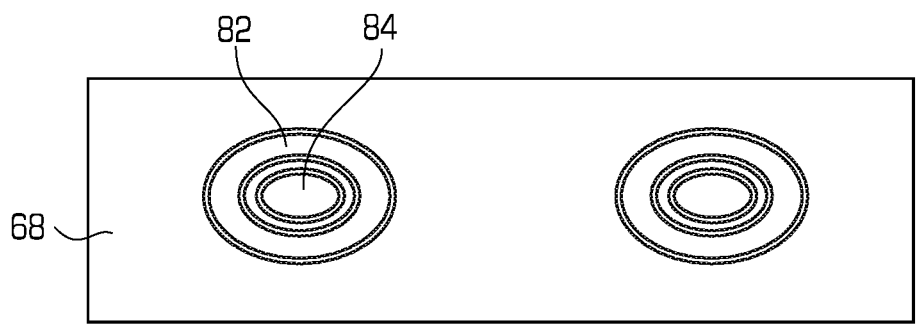

The structure is then covered with a layer of metal 80 (e.g. gold deposited by ALD) which fills the cavities 76 and the holes 78. A metal etch (e.g. CMP or wet etch) is used to remove any of the metal on the top surface of the BARC layer 72. BARC and polymer etches then are used to remove BARC and polymer layers 72, 70, leaving an oval toroid shaped (i.e. donut shaped with a center opening) gold pillar structure 82 surrounding and spaced from an oval gold pillar structure 84 forming an annular (e.g. oval shaped) cavity 86 therebetween. A second dielectric layer 88 is formed over the structure (e.g. HiK or Si based) and in cavities 86, as illustrated in FIGS. 11A and 11B. An etch is used to remove the second dielectric layer 86 on the gold pillar structures 82, 84 and on the first dielectric layer 68, and to recess those portions of the second dielectric layer 88 in cavities 86, resulting in the final structure shown in FIGS. 12A and 12B. NPR 66 includes two top surfaces 82a and 84a and six annular top surface edges, but the second dielectric layer 88 is recessed in cavities 86 and entirely removed outside of cavities 86 (i.e. leaving the first dielectric layer 68 exposed and leaving upper portions of the gold pillar structures 82 and 84 separated by an open gap).

Fourth Embodiment

Figure 13A:
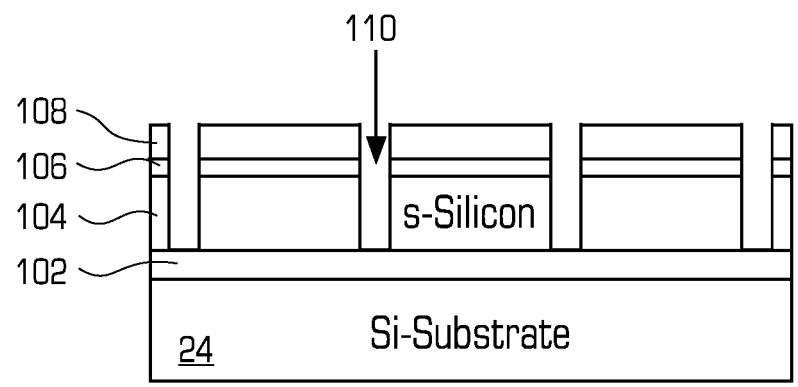
Figure 13B:
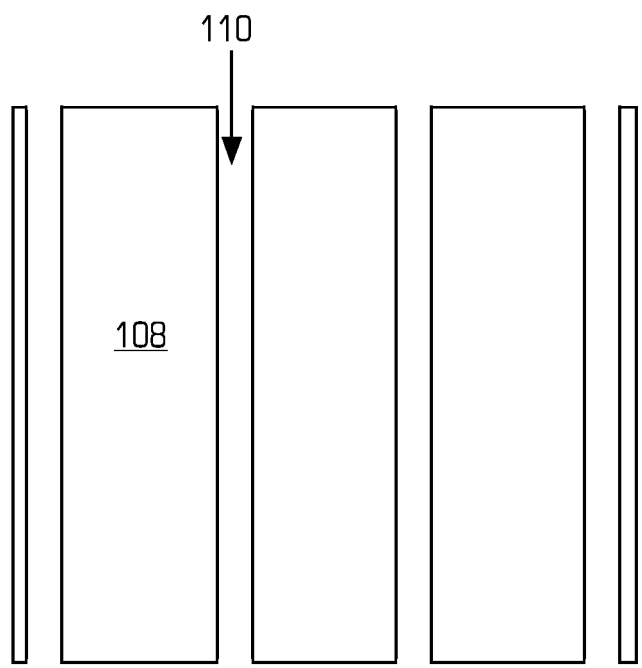

FIGS. 13A-16A and 13B-16B illustrate the photolithographic process used to form the NPR structure 100 according to a fourth embodiment. The process begins by performing a pre-oxidation clean of the substrate 24, following by forming a first dielectric layer 102 (e.g. silicon dioxide—$SiO_2$) over substrate 24 (e.g. Si), for example by thermal oxidation (e.g. 1 µm). This is followed by forming a sacrificial layer 104 over the structure (e.g. silicon that is 100 nm thick). A BARC layer 106 is formed over the sacrificial layer 104. Photo resist 108 is formed over the BARC layer 106, and patterned with parallel trenches 110 approximately 5 nm in width (patterning includes photolithograph exposure and resist etch). BARC and silicon etches are used to extend the trenches 110 down to the first dielectric layer 102. The resulting structure is shown in FIGS. 13A and 13B.

Figure 14A:
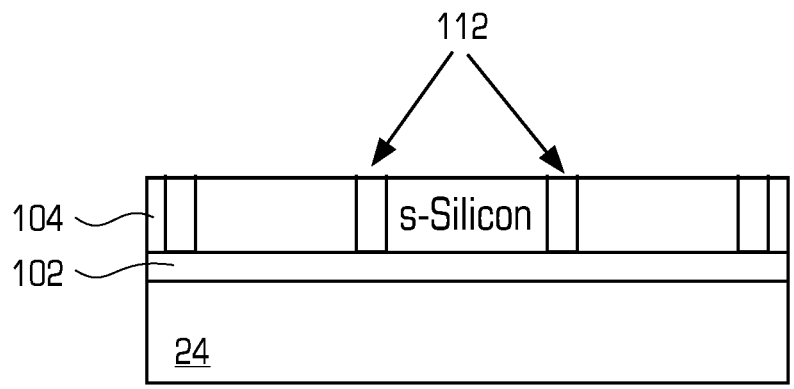
Figure 14B:
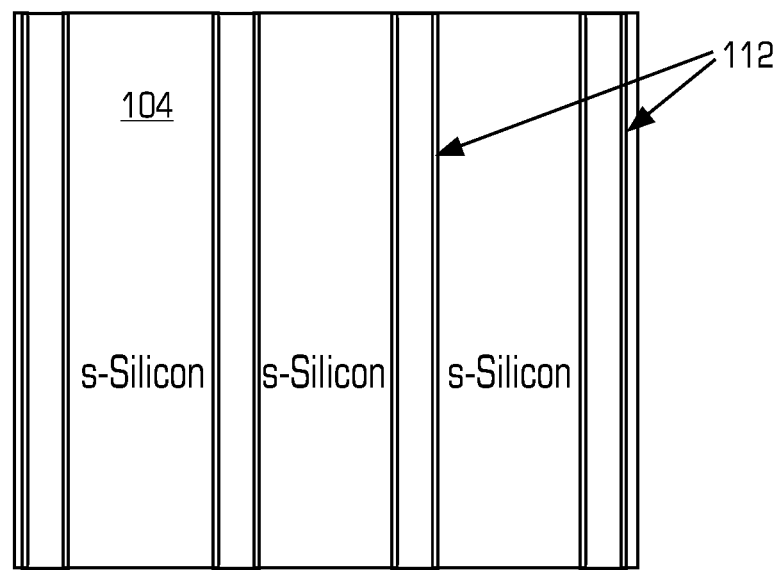

The photo resist 108 and BARC layer 106 are etched away. A second layer of dielectric material 112 is formed over the structure, filling the trenches 110 with the dielectric material 112. A CMP dielectric etch using the sacrificial silicon 104 as an etch stop is used to remove the second layer of dielectric material except for the dielectric material 112 in the trenches, as shown in FIGS. 14A and 14B.

Figure 15A:
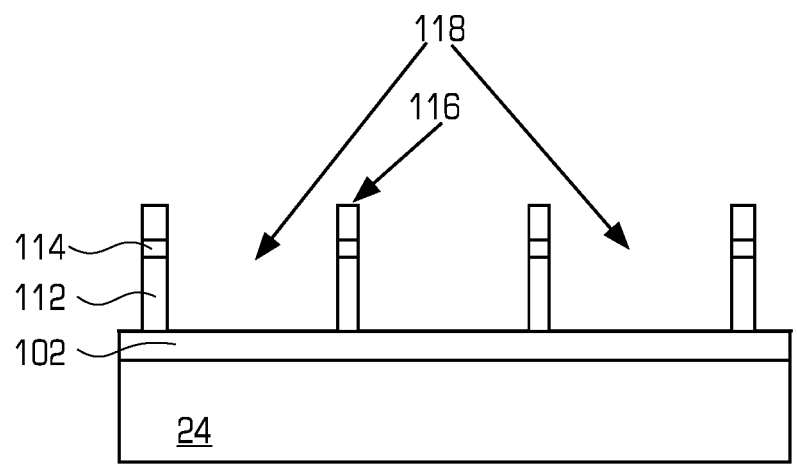
Figure 15B:
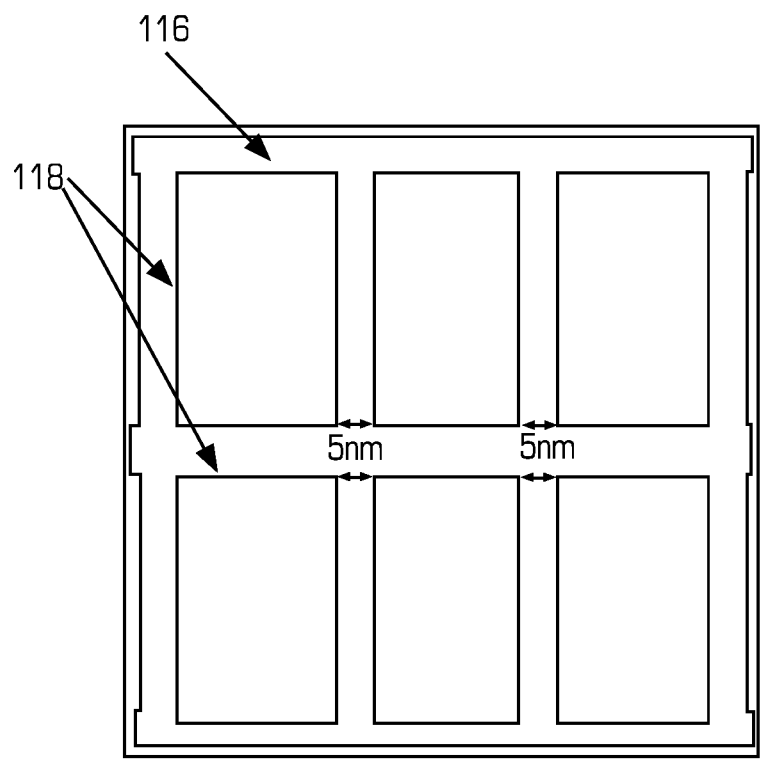

A second BARC layer 114 is formed over the structure. A second photo resist 116 is formed over the BARC layer 114 and patterned leaving columns of photoresist 116 over the dielectric material 112 in filled trenches 110, and rows of photoresist 116 separated by approximately 100 nm. BARC and silicon etches are used to remove the BARC and silicon layers 114, 116 (using the first dielectric layer 102 as an etch stop). These etches result in pillars of the second dielectric 112 extending in the column direction and pillars of the silicon 104 extending in the row direction, leaving cavities 118 extending down to first dielectric 102 formed therebetween, as illustrated in FIGS. 15A and 15B.

Figure 16A:
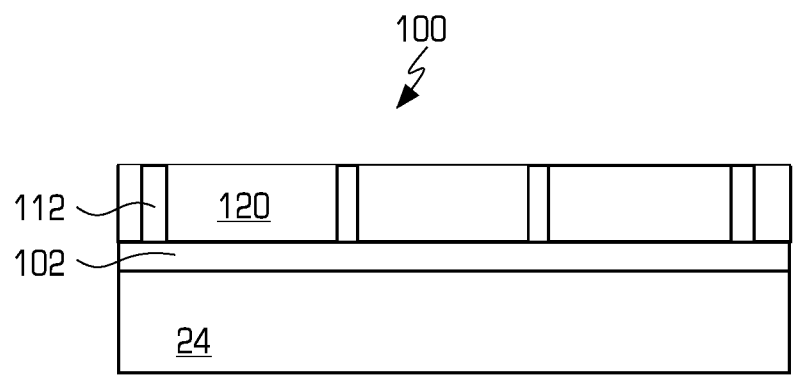
Figure 16B:
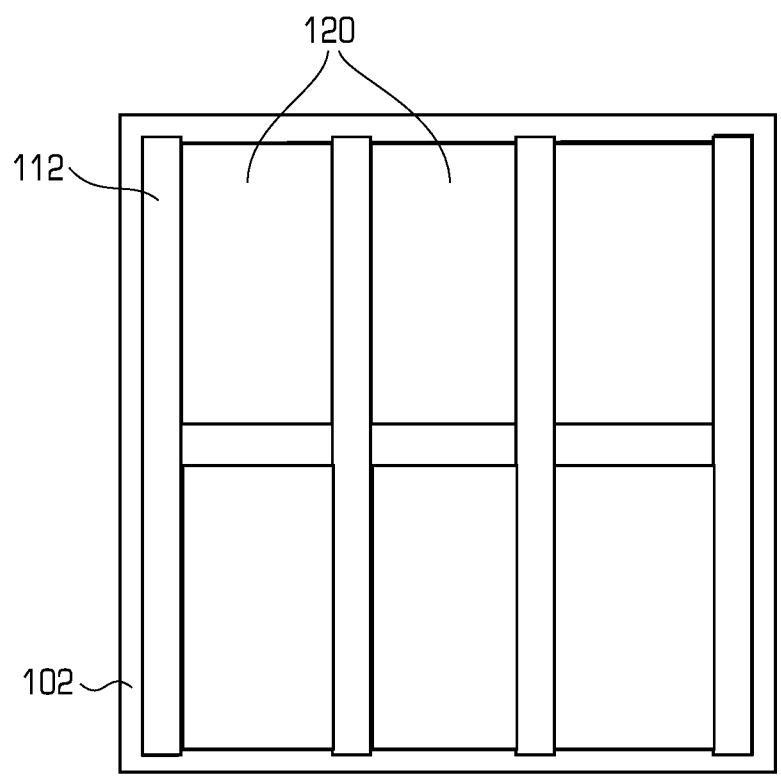

A photo resist and BARC etch is used to remove the remaining photo resist 116 and BARC layer 114. A metal is formed over the structure (e.g. gold), which fills the cavities 118, followed by a metal etch using the dielectric 112 in the filled trenches 110 as an etch stop. A silicon etch is then used to remove the exposed pillars of silicon 104 extending the row direction. The resulting structure is shown in FIGS. 16A and 16B, and includes rows of metal pillars 120 separated by dielectric material 112. The metal pillars 120 are self-aligned to the trenches 110 which were formed in sacrificial silicon layer 104 and filled with dielectric material 112. In contrast to the previous embodiments where the NPR is stacked vertically over the substrate, here the NPR 100 is stacked horizontally over the substrate 24, whereby laterally adjacent metal pillars 120 are separated from each other by dielectric layer 112 thus resonating off each other to form the NPR structure. A preferable non limiting configuration includes one or two rows, and 2 to 20 columns, of the gold pillars 120.

Fifth Embodiment

Figure 17A:
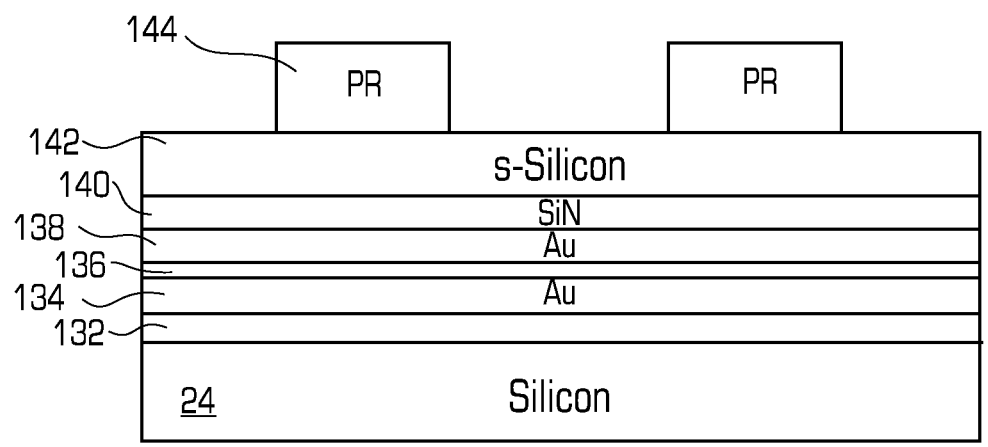
Figure 17B:
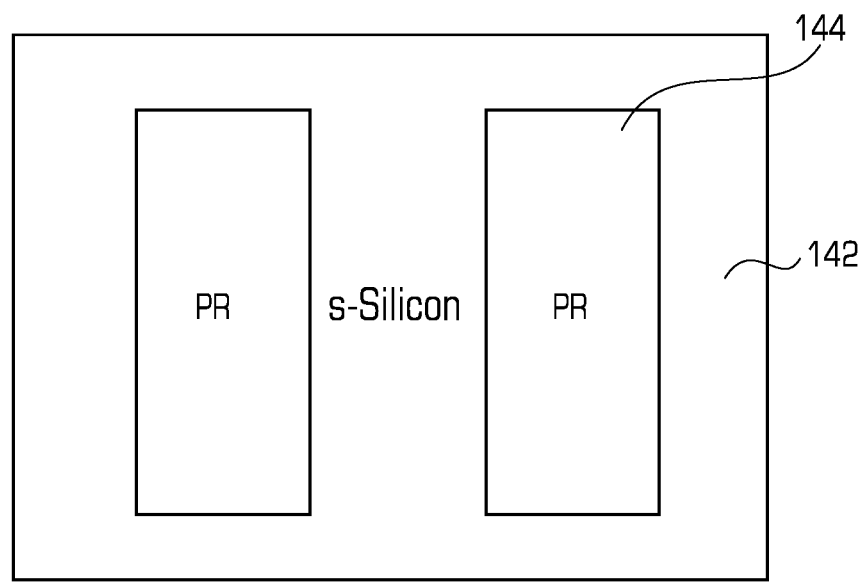

FIGS. 17A-21A and 17B-21B illustrate the photolithographic process used to form the NPR structure 130 according to a fifth embodiment. The process begins by forming a first dielectric layer 132 (e.g. silicon dioxide—$SiO_2$) over substrate 24 (e.g. Si), followed by forming a first metal layer 134 (e.g. gold—25 nm thick) over the first dielectric layer 132, followed by forming a second dielectric layer 136 (e.g. silicon dioxide—5 nm thick) over the first metal layer 134, followed by forming a second metal layer 138 (e.g. gold—25 nm thick) over the second dielectric layer 136. A third dielectric layer 140 (e.g. SiN) is formed over the second metal layer 138. A sacrificial layer 142 (e.g. silicon) is formed over the third dielectric layer 140. Photo resist 144 is formed over the sacrificial silicon layer 142, and patterned (exposure plus photo resist etch) leaving rectangular or oval blocks of photo resist on the structure, as shown in FIGS. 17A and 17B.

Figure 18A:
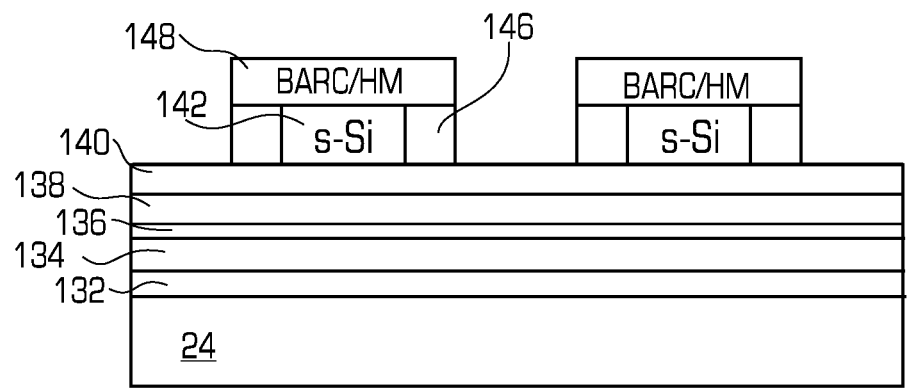
Figure 18B:
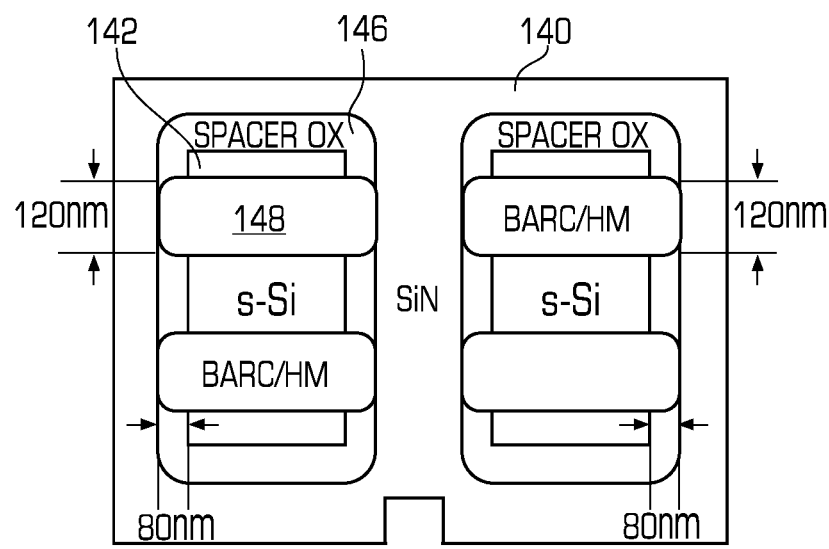
Figure 19A:
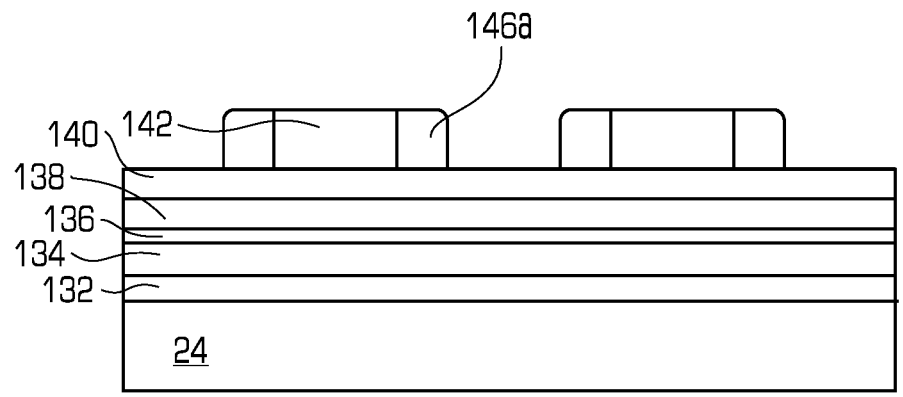
Figure 19B:
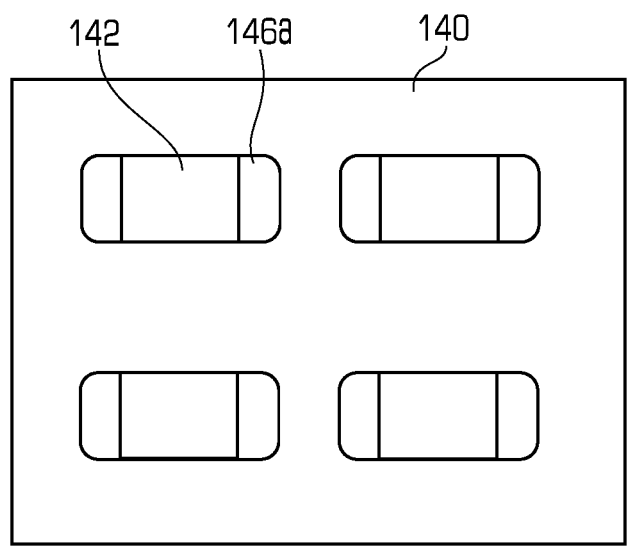

A silicon etch is used to remove the sacrificial silicon 142 except for blocks thereof underneath the blocks of photo resist 144. After the photo resist 144 is removed, a fourth layer of dielectric material (e.g. silicon oxide) is formed over the structure, followed by an oxide etch that removes the silicon oxide except for spacers 146 thereof around the sacrificial silicon blocks. Formation of spacers is well known in the art, and involves the deposition of a material over the contour of a structure, followed by an anisotropic etch process, whereby the material is removed from horizontal surfaces of the structure, while the material remains largely intact on vertically 20 oriented surfaces of the structure. A layer of BARC/HM 148 is formed over the structure, along with another photo resist layer, which is patterned to form a pair of blocks for each block of sacrificial silicon 142 that extend across the width of the sacrificial silicon block. A BARC/HM etch removes those portions of BARC/HM layer 148 not protected by the blocks of photo resist. FIGS. 18A and 18B show the resulting structure after the photo resist 150 is removed.

Figure 20A:
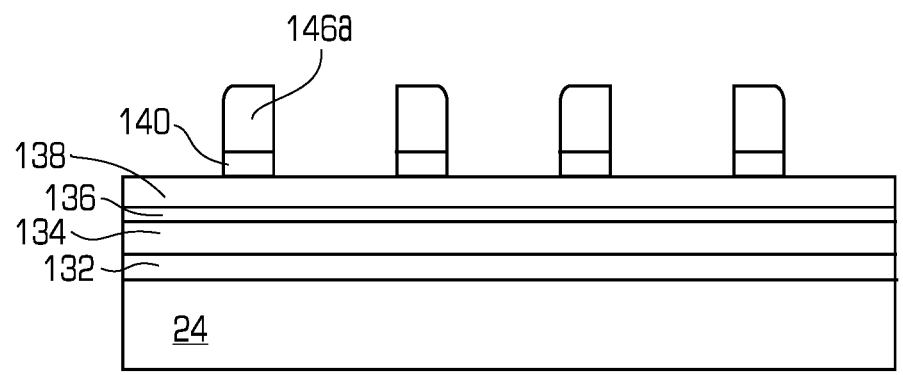
Figure 20B:
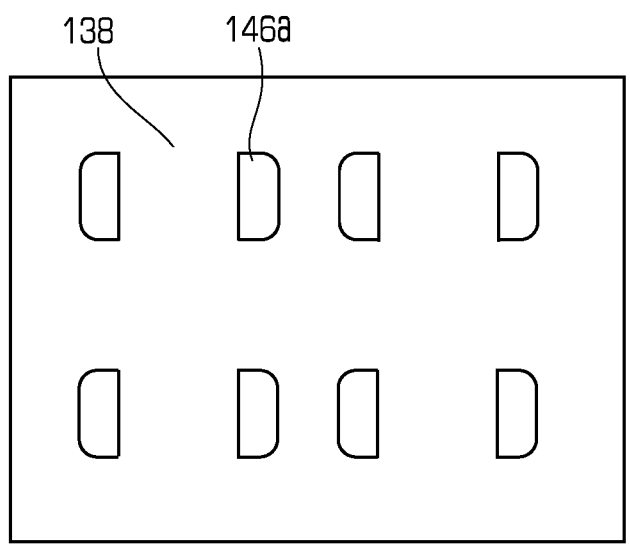
Figure 21A:
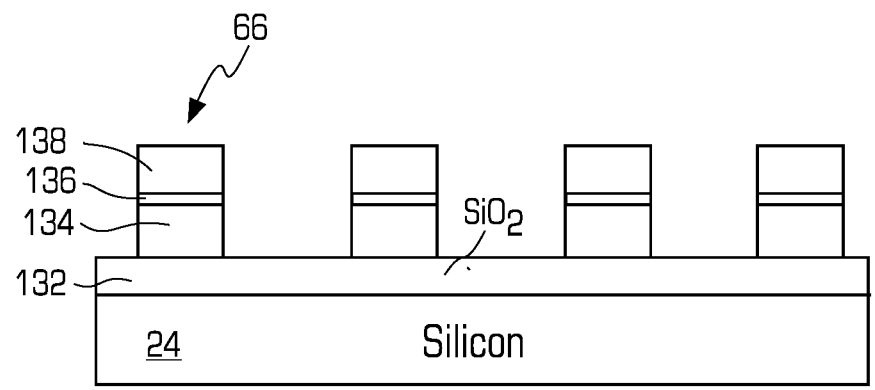
Figure 21B:
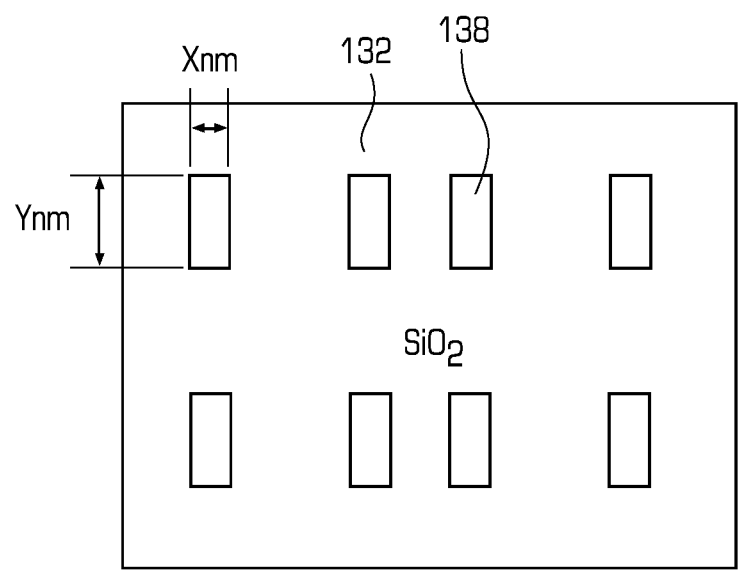

Oxide and silicon etch(es) are performed to remove those portions of the sacrificial silicon 142 and oxide spacer 146 not protected by the BARC/HM blocks 148, leaving discrete (separate) spacers 146a. The BARC/HM blocks 148 are then removed, with the resulting structure shown in FIGS. 19A and 19B. A silicon etch is used to remove the remaining portions of the sacrificial silicon layer 142. A SiN etch is used to remove the exposed portions of the SiN layer 140, exposing selective portions of the second metal layer 138, as shown in FIGS. 20A and 20B.

Gold and dielectric etches are performed to remove those portions of the first and second metal layers 134, 138 (and the dielectric 136 therebetween) not protected by the oxide spacers 146a. The spacers 146 and SiN 140 underneath are then etched away, resulting in the final NPR 130 structure of FIGS. 20A and 20B. With this embodiment, rectangular or oval SERS structures are formed using two lithography masks, whereby smaller NPR structural dimensions can be achieved (i.e. smaller dimensions that the lithography resolution used to make them) because the dimensions of the NPRs 130 are dictated by the size of spacers 146a.

It is to be understood that the present invention is not limited to the embodiment(s) described above and illustrated herein, but encompasses any and all variations falling within the scope of the appended claims. For example, materials, processes and numerical examples described above are exemplary only, and should not be deemed limiting. Further, single layers of material could be formed as multiple layers of such or similar materials, and vice versa. The number of interleaving gold and insulation layers in each embodiment can vary from the number shown and described. Finally, while it is preferable to include insulation layer 22, 46, 68, 102, 132 between the substrate and first gold layer, the NPR's could be formed directly on a non-conducting substrate or on such a substrate using an intervening conductive layer that assists the adhesion of the gold layer.

It should be noted that, as used herein, the terms "over" and "on" both inclusively include "directly on" (no intermediate materials, elements or space disposed therebetween) and "indirectly on" (intermediate materials, elements or space disposed therebetween). Likewise, the term "adjacent" includes "directly adjacent" (no intermediate materials, elements or space disposed therebetween) and "indirectly adjacent" (intermediate materials, elements or space disposed there between). For example, forming an element "over a substrate" can include forming the element directly on the substrate with no intermediate materials/elements therebetween, as well as forming the element indirectly on the substrate with one or more intermediate materials/elements therebetween.

What is claimed is:

1. A nanoplasmonic resonator (NPR), comprising:
a substrate;
a first metallic member disposed on the substrate;
a second metallic member spaced apart from the first metallic member; and
a first insulation layer at least partially disposed between the first and second metallic members;
wherein the first insulation layer includes at least one of:
a notch formed laterally therein such that there is an open gap separating outer edge portions of the first and second metallic members, and
at least a portion thereof having a toroid shape.

2. The nanoplasmonic resonator (NPR) of claim 1, wherein the first and second metallic members have an oval shape.

3. The nanoplasmonic resonator (NPR) of claim 1, further comprising:
a second insulation layer disposed between the substrate and the first metallic member.

4. The nanoplasmonic resonator (NPR) of claim 1, wherein the first insulation layer includes a notch formed laterally therein such that there is an open gap separating outer edge portions of the first and second metallic members, and wherein the second metallic member is disposed over the first metallic member and the substrate.

5. The nanoplasmonic resonator (NPR) of claim 1, wherein the first metallic member is toroid-shaped with a center opening, and wherein the second metallic member is disposed at least partially in the center opening.

6. The nanoplasmonic resonator (NPR) of claim 5, wherein the first insulation layer is disposed in a lower portion of the center opening but not in an upper portion of the center opening such that upper portions of the first and second metallic members are separated by an open gap.

7. A The nanoplasmonic resonator (NPR), comprising:
a substrate;
a first metallic member disposed on the substrate;
a second metallic member spaced apart from the first metallic member; and
a first insulation layer at least partially disposed between the first and second metallic members;
wherein the first insulation layer includes at least one of:
a notch formed laterally therein such that there is an open gap separating outer edge portions of the first and second metallic members,
at least a portion thereof having a toroid shape, and
a length extending between the first and second metallic members which are laterally adjacent to each other;
wherein the first metallic member includes a cavity formed into an upper surface thereof, and
wherein the second metallic member is disposed at least partially in the cavity;
wherein the first insulation layer is disposed in a lower portion of the cavity but not in an upper portion of the cavity such that upper portions of the first and second metallic members are separated by an open gap.

8. A method of fabricating a nanoplasmonic resonator (NPR), comprising:
forming a first metallic member on a substrate;
forming a second metallic member spaced apart from the first metallic member;
forming a first insulation layer at least partially disposed between the first and second metallic members, wherein the first insulation layer includes at least one of:
a notch formed laterally therein such that there is an open gap separating outer edge portions of the first and second metallic members, and
at least a portion thereof having a toroid shape.

9. The method of claim 8, wherein the first and second metallic members have an oval shape.

10. The method of claim 8, further comprising:
forming a second insulation layer disposed between the substrate and the first metallic member.

11. The method of claim 8, wherein the second metallic member is disposed over the first metallic member and the substrate, wherein the first insulation layer includes a notch formed laterally therein such that there is an open gap separating outer edge portions of the first and second metallic members, and wherein the forming of the first insulation layer to include the notch comprises performing an isotropic etch.

12. The method of claim 8, wherein the forming of the first and second metallic members and the first insulation layer comprises:
forming a layer of sacrificial material on the substrate;
forming first and second cavities into a top surface of the sacrificial material, wherein the second cavity is toroid shaped and surrounds the first cavity;
forming metallic material in the first cavity to form the first metallic member and the second cavity to form the second metallic member;
removing the sacrificial material such that an annular cavity is left between the first and second metallic members; and
forming insulation material in the annular cavity to form the first insulation layer.

13. The method of claim 12, wherein the forming of the first insulation layer further comprises:
removing a portion of the first insulation layer disposed in the annular cavity such that upper portions of the first and second metallic members are separated by an open gap.

14. The method of claim 12, wherein the sacrificial material is a polymer.

15. A method of fabricating a nanoplasmonic resonator (NPR), comprising:
  forming a first metallic member on a substrate;
  forming a second metallic member spaced apart from the first metallic member;
  forming a first insulation layer at least partially disposed between the first and second metallic members, wherein the first insulation layer includes at least one of:
    a notch formed laterally therein such that there is an open gap separating outer edge portions of the first and second metallic members,
    at least a portion thereof having a toroid shape, and
    a length extending between the first and second metallic members which are laterally adjacent to each other;
  wherein the forming of the first and second metallic members and the first insulation layer comprises:
    forming a layer of sacrificial material on the substrate;
    forming a cavity into a top surface of the sacrificial material;
    lining the cavity with metallic material to form the first metallic member;
    forming insulation material in the cavity and on the first metallic member to form the first insulation layer;
    forming metallic material in the cavity and on the first insulation layer to form the second metallic member; and
    removing the sacrificial material; and
  wherein the forming of the first insulation layer further comprises:
    removing a portion of the first insulation layer disposed in an upper portion of the cavity such that upper portions of the first and second metallic members are separated by an open gap.

16. The method of claim 15, wherein the sacrificial material is a polymer.

17. A method of fabricating a nanoplasmonic resonator (NPR), comprising:
  forming a first metallic member on a substrate;
  forming a second metallic member spaced apart from the first metallic member;
  forming a first insulation layer at least partially disposed between the first and second metallic members, wherein the first insulation layer includes at least one of:
    a notch formed laterally therein such that there is an open gap separating outer edge portions of the first and second metallic members,
    at least a portion thereof having a toroid shape, and
    a length extending between the first and second metallic members which are laterally adjacent to each other;
  wherein the forming of the first and second metallic members and the first insulation layer comprises:
    forming a layer of sacrificial material on the substrate;
    forming parallel trenches into the layer of sacrificial material;
    forming insulation material in the trenches to form parallel lines of the first insulation layer;
    removing the sacrificial material such that cavities are left between the parallel lines of the first insulation layer;
    forming metal material in the cavities to form the first and second metallic members such that the first and second metallic members are laterally adjacent to each other with the first insulation layer disposed therebetween.

18. The method of claim 17, wherein the sacrificial material is silicon.

19. A method of fabricating a nanoplasmonic resonator (NPR), comprising:
  forming a first metallic member on a substrate;
  forming a second metallic member spaced apart from the first metallic member;
  forming a first insulation layer at least partially disposed between the first and second metallic members, wherein the first insulation layer includes at least one of:
    a notch formed laterally therein such that there is an open gap separating outer edge portions of the first and second metallic members,
    at least a portion thereof having a toroid shape, and
    a length extending between the first and second metallic members which are laterally adjacent to each other;
  wherein the forming of the first and second metallic members and the first insulation layer comprises:
    forming a first layer of metallic material on the substrate;
    forming the first insulation layer on the first layer of metallic material;
    forming a second layer of metallic material on the first insulation layer;
    forming blocks of sacrificial material on the second layer of metallic material;
    forming discrete spacers along sidewalls of the blocks of sacrificial material;
    removing the sacrificial material;
    performing an etch through the first and second layers of metallic material and the first insulation layer to remove these layers except for portions thereof directly under the discrete spacers, wherein the first and second metallic members and the first insulation layer are disposed under one of the discrete spacers.

20. The method of claim 19, further comprising:
removing the discrete spacers.

* * * * *